(12) United States Patent
Yang et al.

(10) Patent No.: US 7,691,575 B2
(45) Date of Patent: Apr. 6, 2010

(54) IMMUNOMODULATORY COMPOSITIONS

(75) Inventors: Wen-Chin Yang, Taichung County (TW); Shu-Lin Chang, Hsin-Chu (JP); Yi-Ming Chiang, Taipei County (TW); Lie-Fen Shyur, Taipei (TW)

(73) Assignee: Academia Sinica, Taipei (TW)

( * ) Notice: Subject to any disclaimer, the term of this patent is extended or adjusted under 35 U.S.C. 154(b) by 75 days.

(21) Appl. No.: 11/215,568

(22) Filed: Aug. 29, 2005

(65) Prior Publication Data

US 2007/0048394 A1 Mar. 1, 2007

(51) Int. Cl.
*C12Q 1/68* (2006.01)
*C12N 15/63* (2006.01)
*C12N 5/00* (2006.01)
*C07H 21/04* (2006.01)
*C07K 1/00* (2006.01)

(52) U.S. Cl. .................... 435/6; 435/455; 435/325; 435/320.1; 536/24.1

(58) Field of Classification Search ............... None
See application file for complete search history.

(56) References Cited

U.S. PATENT DOCUMENTS

2003/0170656 A1* 9/2003 Cen et al. ................. 435/6

OTHER PUBLICATIONS

Young et al. (1986) J. Immunol. 136:4700-4703.*
NCBI Entrez database entry AF375790, www.ncbi.nlm.nih.gov/entrez/viewer.fcgi?db=nuccore&id=14278712, published Jun. 1, 2000, downloaded Aug. 31, 2007.*
Wang et al. (2003) J. Biol. Chem. 278:37622-37631.*
Penix et al. (1993) J. Exp. Med. 178:1483-1496.*
Young, H.A. Regulation of Interferon-gamma gene expression. Journal of Interferon and Cytokine Research 16:563-568, 1996.*
Bhatti et al. "Transcriptional regulation by retinoic acid of interleukin-2 alpha receptor in human B cells". Immunology 81(2):273-279, Feb. 1994 (abstract only).
Becker et al. "Negative transcriptional regulation in anergic T cells". Proc. Natl. Acad. Sci. USA 92:2375-2378, Mar. 1995.
Beiqing et al. "Sublethal levels of oxidative stress stimulate transcriptional activation of c-jun and suppress IL-2 promoter activation in Jurkat T cells". J. Immunol. 157(1):160-169, Jul. 1996 (abstract only).
Felli et al. "Retinoic Acid-Induced Down-Regulation of the Interleukin-2 Promoter via Cis-Regulatory Sequences Containing an Octamer Motif". Molecular and Cellular Biology 11(9):4771-4778, Sep. 1991.
Soutto et al. "A Minimal IFN-$\gamma$ Promoter Confers Th1 Selective Expression". The Journal of Immunology 169:4205-4212, 2002.
Suzuki et al. "The Human IL-2 Receptor Gene Contains a Positive Regulatory Element That Functions in Cultured Cells and Cell-free Extracts". The Journal of Biological Chemistry 262(11):5079-5086, 1987.

* cited by examiner

*Primary Examiner*—Quang Nguyen
(74) *Attorney, Agent, or Firm*—Occhiuti Rohlicek & Tsao LLP

(57) ABSTRACT

Methods useful, for example, in identifying plant compositions that have immunomodulatory activity. Also disclosed is an Asteraceae plant immunomodulatory composition useful for increasing an immune response, e.g., IFN $\gamma$ or IL-2 transcription.

3 Claims, No Drawings

IMMUNOMODULATORY COMPOSITIONS

BACKGROUND

T-cells play a pivotal role in cellular and humoral immune response and can mediate the functions of other immune system cells (e.g., B-cells, leukocytes, or macrophages). Type I and type II helper T-cells are regulated by autocrine and paracrine factors such as cytokines, a class of secreted immunomodulatory proteins expressed primarily in T-cells.

Cytokines are implicated in immune responses, including proliferation, activation, and differentiation of T-cells. For example, interferon γ (IFN γ) stimulates inflammation, antitumoral response, antiviral response, and T-cell differentiation. Interleukin 2 (IL-2), secreted by activated T-lymphocytes, is essential for T-cell function. Thus, cytokines are powerful immunostimulants, and can be administered exogenously to stimulate an immune response in a patient. However, administering an exogenous cytokine presents a number of difficulties. First, the production of large quantities of high purity cytokines is technically demanding and very expensive. Second, due to their lability, cytokines must be prevented from degrading or inactivating before use. Finally, an exogenous cytokine may trigger an allergic reaction.

Thus, there is a need for inexpensive and stable compositions for increasing endogenous cytokine levels, as well as methods for identifying and using such compositions.

SUMMARY

The present invention is based on the unexpected finding that Asteraceae plant extract compositions modulate an immune response.

Accordingly, one aspect of the invention is a method for identifying a composition (e.g., a plant extract or a pure compound) for modulating an immune response. The method includes (1) providing a cell (e.g., a T-cell) which includes an isolated nucleic acid containing the sequence of SEQ ID NO:1 (an IFN γ promoter) or SEQ ID NO:2 (an IL-2 promoter) operably linked to a sequence encoding a reporter polypeptide, (2) contacting the cell with a test composition, and (3) assaying the expression level or activity of the encoded reporter polypeptide. If the test composition increases the expression level or activity of the encoded reporter polypeptide, relative to a negative control treatment, then the test composition modulates an immune response. The term "immune response" refers to any phenotypic alteration related to immune function (e.g., a change in IFN γ or IL-2 promoter activity) occurring in one or more cells which are either of immune system lineage or respond to a given stimulus with a phenotypic alteration analogous to that of a cell of immune system lineage ex vivo or in vivo. The term "isolated nucleic acid" refers to a nucleic acid the structure of which is not identical to that of any naturally occurring nucleic acid.

Another aspect of the invention is a composition containing an Asteraceae plant extract (e.g., a *Bidens pilosa* extract), which increases an immune response (e.g., increases transcription from an IFN ι or an IL-2 promoter), and, in dried form, is soluble in dimethyl sulfoxide at 15 to 37° C. The Asteraceae plant extract may contain centaurein, and, in dried form, may be soluble in butanol at 15 to 37° C. The just-mentioned composition (e.g., pure centaurein) can be used to increase an IFN γ or IL-2 level in a cell (e.g., a T-cell). Indeed, an effective amount of this composition can be administered to a subject in need to increase an immune response in the subject. Preferably, a subject is diagnosed as needing an increased immune response prior to treatment. This composition can also be used for the manufacture of a medicament for increasing an immune response in a subject.

Other features or advantages of the present invention will be apparent from the following detailed description, and also from the claims.

DETAILED DESCRIPTION

Methods are described below for identifying immunomodulatory compositions (e.g., a *Bidens pilosa* extract) and using them to increase an IFN γ or IL-2 level in a cell, ex vivo or in vivo.

Compositions (e.g., a plant extract or a pure compound) that modulate an immune response can be identified with an IFN γ or IL-2 promoter reporter assay. A test reporter construct is first generated by fusing each promoter to a nucleic acid encoding a reporter polypeptide. The test reporter construct is then introduced into a host cell whereby the promoter controls expression of the reporter polypeptide in the host cell. Promoter activity can be quantified by measuring a property of the reporter polypeptide (e.g., enzymatic activity or fluorescence), reporter polypeptide expression (e.g., by an ELISA assay), or reporter mRNA expression (e.g., by a fluorescent hybridization technique). IFN γ or IL-2 promoter activity is compared between a first group exposed to a test composition and a second group exposed to a negative control treatment. If reporter activity or expression is increased in the first group relative to the second group, then the test composition is identified as immunomodulatory.

An IFN γ promoter test reporter construct can include a promoter sequence of SEQ ID NO:1 as follows:

```
                                             (SEQ ID NO: 1)
GGACTTCCTCACCAAATTGTTCTTTTAACCGCATTCTTTCCTTGCTTTCT

GGTCATTTGCAAGAAAAATTTTAAAAGGCTGCCCCTTTGTAAAGGTTTGA

GAGGCCCTAGAATTTCGTTTTTCACTTGTTCCCAACCACAAGCAAATGAT

CAATGTGCTTTGTGAATGAAGAGTCAACATTTTACCAGGGCGAAGTGGGG

AGGTACAAAAAAATTTCCAGTCCTTGAATGGTGTGAAGTAAAAGTGCCTT

CAAAGAATCCCACCAGAATGGCACAGGTGGGCATAATGGGTCTGTCTCAT

CGTCAAAGGACCCAAGGAGTCTAAAGGAAACTCTAACTACAACACCCAAA

TGCCACAAAACCTTAGTTATTAATACAAACTATCATCCCTGCCTATCTGT

CACCATCTCATCTTAAAAAACTTGTGAAAATACGTAATCCTCAGGAGACT

TCAATTAGGTATAAATACCAGCAGCCAGAGGAGGTGCAGCACATTGTTCT

GATCATCTGAAGATCAGCTATTAGAAGAGAAAGATCAGTTAAGTCCTTTG

GACCTGATCAGCTTGATACAAGAACTACTGATTTCAACTTCTTTGGCTTA

ATTCTCTCGGAAACG
```

An IL-2 promoter test reporter construct can include the sequence of SEQ ID NO:2 as follows:

```
                                             (SEQ ID NO: 2)
CACCACAATATGCTATTCACATGTTCAGTGTAGTTTTATGACAAAGAAAA

TTTTCTGAGTTACTTTTGTATCCCCACCCCCTTAAAGAAAGGAGGAAAAA

CTGTTTCATACAGAAGGCGTTAATTGCATGAATTAGAGCTATCACCTAAG

TGTGGGCTAATGTAACAAAGAGGGATTTCACCTACATCCATTCAGTCAGT
```

-continued

CTTTGGGGGTTTAAAGAAATTCCAAAGAGTCATCAGAAGAGGAAAAATGA

AGGTAATGTTTTTTCAGACAGGTAAAGTCTTTGAAAATATGTGTAATATG

TAAAACATTTTGACACCCCCATAATATTTTTCCAGAATTAACAGTATAAA

TTGCATCTCTTGTTCAAGAGTTCCCTATCACTCTCTTTAATCACTACTCA

CAGTAACCTCAACTCCTGCCACA

A skilled artisan will recognize that other structurally and functionally equivalent promoters can be used in just-described promoter reporter assays, e.g., promoters that are at least 90% (i.e., any value between 90% and 100%) identical to either SEQ ID NO:1 or SEQ ID NO:2. Examples include promoters with deletions or additions of up to 40 nucleotides and retaining at least 80% of the promoter activity of SEQ ID NO:1 or SEQ ID NO:2. Uses of such promoters are also within the scope of the claimed invention.

Suitable reporter polypeptides include, e.g., firefly luciferase, *renilla* luciferase, fluorescent proteins (e.g., enhanced green fluorescent protein), β-galactosidase, β-lactamase, alkaline phosphatase, and horseradish peroxidase. For example, luciferase activity can be detected by providing an appropriate luminogenic substrate, e.g., firefly luciferin for firefly luciferase or coelenterazine for *Renilla* luciferase. Luciferase activity in the presence of an appropriate substrate can be quantified by luminometry.

A second reporter construct, i.e., a "normalization reporter construct," can also be used. The normalization reporter polypeptide encoded by the normalization reporter construct generally has an activity that is distinct from that of the test reporter polypeptide. Further, the normalization reporter construct generally includes a weak constitutive promoter, e.g., the herpes thymidine kinase (HTK) promoter that drives expression of the reporter polypeptide. The normalization reporter construct can be separate from or part of the same nucleic acid that includes the first reporter construct (e.g., as part of one plasmid). Promoter activity can be quantified by taking the ratio of test reporter polypeptide activity to normalization reporter polypeptide activity. For example, in a dual luciferase reporter assay, firefly luciferase can serve as the test reporter polypeptide and *Renilla* luciferase can serve as a normalization reporter polypeptide. Details of the dual luciferase assay, including high-throughput methods, are disclosed in U.S. Pat. No. 5,744,320. Suitable cells for the disclosed promoter reporter assays include any cells derived from a T-cell lineage, e.g., cells from human cell lines such as Jurkat cells, HH cells, or T1 cells, as well as primary T-lymphocytes. Methods for generating reporter constructs, introducing them into cells, and assaying various reporter polypeptide activities, can be found in detail in, e.g., *Current Protocols in Molecular Biology*, John Wiley & Sons, N.Y (2005), 3.16-3.17 and 9.1-9.14, respectively).

Reporter expression or activity can be assayed in a cell free assay (e.g., a cell lysate) or in live cells, depending on the reporter polypeptides or reporter enzyme substrates selected for the assay. Cell free assays can be conducted in any suitable vessel (e.g., microtiter plates, test tubes, cuvettes, and microcentrifuge tubes). Live cell assays can be conducted in any vessel suitable for mammalian cell culture (e.g., microtiter cell culture plates, multiwell plates, cell culture dishes, and cell culture flasks). Multi-well cell culture plates can be adapted for direct luminometry or fluorimetry of cells or cell lysates in the wells of the plate. Luciferase activity can be measured in live cells by adding a suitable luciferase substrate directly to the cultured cells in cell culture medium (i.e., without a lysis step) and measuring light emission directly from the intact cells. Viviren™ substrate (Promega, Wis.) or other suitable cell-permeable luciferase substrates can be added directly to cells to measure luciferase activity.

Fluorescent polypeptides (e.g., EGFP) can be detected and quantified in live cells by a number of detection methods known in the art (e.g., fluorimetry or fluorescence microscopy). Details of reporter assays screens in live cells using fluorescent polypeptides, including high-throughput methods, can be found, e.g., in U.S. Pat. No. 6,875,578.

The promoter reporter assays described above can be used to identify compositions (e.g., plant extracts or pure compounds) that have immunomodulatory activity. Identified immunomodulatory compositions (e.g., a plant extract containing centaurein) can be used to increase IFN γ or IL-2 levels in a cell. For example, IFN γ or IL-2 expression can be increased in T-cells or T-cell progenitors ex vivo, before infusion into a subject. Alternatively, an effective amount of an immunomodulatory plant extract can be administered directly to a subject to increase endogenous expression of IFN γ or IL-2 in cells in vivo. For example, an Asteraceae plant extract composition containing centaurein can be used prophylactically or therapeutically to stimulate an immune response in a subject in need thereof. The subject is typically at risk of or suffering from an immunodeficiency or one or more conditions that can be ameliorated by an elevated IFN γ or IL-2 level. Examples of such conditions include, but are not limited to viral infections (e.g., by hepatitis B or C), the presence of tumors, osteopetrosis, and Th2-mediated autoimmune diseases.

IFN γ or IL-2 expression can readily be determined in cells treated with immunomodulatory compositions ex vivo or in vivo. For example, expression of mRNA in a biological sample (e.g., a cell culture or a blood sample) can be monitored by standard RNA blot analysis or can be aided by PCR, especially quantitative PCR (qPCR) or similar techniques known in the art (see, e.g., *Current Protocols in Molecular Biology*, John Wiley & Sons, N.Y. (2005), 15.5-15.7). Immunoassays can also be used to detect or monitor IFN γ or IL-2 polypeptide levels in a biological sample. IFN γ or IL-2-specific polyclonal or monoclonal antibodies are commercially available and may be used in any standard immunoassay format. Useful assays for measuring IFN γ or IL-2 polypeptide levels include competitive and non-competitive assays, radioimmunoassays, bioluminescence and chemiluminescence assays, fluorometric assays, sandwich assay, dot blots, enzyme linked assays (including ELISA), microtiter plates, and antibody coated strips or dipsticks for rapid monitoring of blood. For each method, the range, sensitivity, precision, reliability, specificity and reproducibility of the assay is established. Examples of some immunoassays are described in detail in, e.g., *Current Protocols in Molecular Biology*, John Wiley & Sons, N.Y. (2005), 11.1-11.3.

Plant extracts containing centaurein or centaurein itself can be incorporated into pharmaceutical compositions for prophylactic or therapeutic use. For example, a pharmaceutical composition can include an effective amount of centaurein and a pharmaceutically acceptable carrier. The term "an effective amount" refers to the amount of an active composition that is required to confer a prophylactic or therapeutic effect on the treated subject. Effective doses will vary, as recognized by those skilled in the art, depending on the types of diseases treated, the severity of the diseases, the general health and/or age of the subject, previous treatments, route of administration, excipient usage, and the possibility of co-usage with other prophylactic or therapeutic treatment.

To practice the method of the present invention, an active composition can be administered parenterally, orally, nasally, rectally, topically, or buccally. The term "parenteral" as used herein refers to subcutaneous, intracutaneous, intravenous, intramuscular, intra-articular, intra-arterial, intrasynovial, intrastemal, intrathecal, or intralesional, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

An active composition can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active centaurein compound. Examples of other carriers include colloidal silicon oxide, magnesium stearate, cellulose, sodium lauryl sulfate, and D&C Yellow # 10.

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

Preparation of *Bidens pilosa* Extract and Centaurein

Whole *B. pilosa* plants (1.2 kg) were ground and extracted twice with nine liters of boiling water. The two resulting solutions were pooled and lyophilized, yielding 66.4 g of a crude extract that was then resuspended in one liter of water. The aqueous resuspended extract was then serially extracted with ethyl acetate (EA) and butanol (BuOH) (1 L×3 for each partitioning). The aqueous, EA, and BuOH fractions were lyophilized, yielding 0.8 g of EA extract, 9.3 g of BuOH extract, and 56.2 g of aqueous extract.

Analytical chromatography of the BuOH extract was performed on a RP-18 silica gel open column with a methanol/water gradient solvent system. Two compounds, 4,5-di-O-caffeoylquinic acid and centaurein, were found to be enriched in the fractions eluted with 30% and 50% methanol, respectively. They were further purified on a Luna 5μ C18(2) HPLC column (Phenomenex) using a Jasco HPLC system equipped with a PU-1580 pump and a UV-1575 UV/VIS detector. 4,5-di-O-caffeoylquinic acid and centaurein were eluted using 15% and 25% methylcyanide, respectively.

The identities of 4,5-di-O-caffeoylquinic acid and centaurein were determined with the following analytical methods: melting points were determined with a Yanagimoto micromelting point apparatus. Optical rotations were measured using a JASCO DIP-1000 digital polarimeter. Infrared spectra were recorded on a Perkin-Elmer 983G spectrophotometer. $^1$H and $^{13}$C NMR spectra were performed on a Varian Unity Plus 400 spectrometer. ESI-MS was performed on a ThermoFinnigan LCQ Advantage ion trap mass spectrometer.

EXAMPLE 2

Screen for Immunomodulatory Activity in Extracts from 46 Plants

Extracts, extract fractions, or purified compounds from as many as 46 plants, prepared as described in Example 1 above, were screened for immunomodulatory activity using a promoter reporter assay as follows.

Jurkat cells were transfected with pIFN γ-Luc and pRL-TK, or pIL-2 and pRL-TK, plasmid DNA constructs using electroporation and then treated with different plant crude extracts, which were prepared using boiling water. The fold induction was expressed in arbitrary units as the ratio of firefly luciferase activity (encoded by pIFN γ-Luc) to that of *Renilla* luciferase (pRL-TK).

Reporter Constructs

A firefly luciferase vector, pcDNAΔCMVLuc, was constructed from the promoterless pcDNA3™ vector (Invitrogen, Calif.) linked to a firefly luciferase gene derived from the pGL31uc™ vector (Promega, Wis.). Plasmid pRL-TK containing the thymidine kinase promoter linked to a *Renilla* luciferase reporter gene was purchased from Promega.

A 615 base pair (bp) DNA fragment containing the human IFN γ promoter region from bp −487 to +128 (SEQ ID NO:1) was amplifed by polymerase chain reaction (PCR) using the specific primers (5'-GGACTTCCTCACCAAATTGTT-3' (SEQ ID NO:3) and 5'-CGTTTCCGAGAGAATTAAGCC-3' (SEQ ID NO:4))and human genomic DNA, isolated from blood, as a template. The resulting PCR product, which included flanking Eco RI sites, was subcloned into a pcDNAΔCMVLuc vector containing a promoterless firefly luciferase gene to generate the plasmid reporter construct pIFN γ-Luc.

Similarly, the promoter region of the IL-2 gene from bp −376 to +47 (SEQ ID NO:2) was amplified by PCR and a pair of IL-2 primers (5'-CGGGGTACCCACCACAATATGC-TATTCAC-3' (SEQ ID NO:5) and 5'-GCCGGTACCTGTG-GCAGGAGTTGAGGTTAC-3') (SEQ ID NO:6) and then subcloned into pcDNAACMVLuc to generate pIL-2-Luc.

The pIFN γ-Luc and pIL-2-Luc reporter constructs were confirmed by DNA sequencing.

Cell Growth and Gene Transfer

Cells from the Jurkat human T-cell line were grown in RPMI 1640 medium supplemented with 10% fetal bovine serum, penicillin (100 U/mL), streptomycin (100 μg/mL), 2-mercaptoethanol (50 μM), sodium pyruvate (1 mM), and glutamate (292 μg/mL). Jurkat cells were co-transfected with pIFN γ-Luc and pRL-TK plasmids, or pIL-2-Luc and pRL-TK plasmids by electroporation with a Bio-Rad Gene Pulser™ electroporator (Bio-Rad, Calif.) set at 960 μF and 260 V. After a two hour recovery period, the transfected T-cells were: left untreated (i.e., serving as the negative control group), treated with phytohemagglutinin (i.e., serving as the positive control group), or treated with a plant extract, extract fraction, or pure compound at various concentrations (i.e., serving as the experimental test group).

Promoter Reporter Assay

Firefly and *Renilla* luciferase activities were measured in cell lysates made from transfected T-cells that were exposed to a plant extract or phytocompound, or underwent negative control treatment. Cell lysates were prepared by lysing the transfected cells in passive lysis buffer (Promega, Wis.). The protein concentration in each lysate was determined using a Bradford reagent protein assay (Bio-Rad, Calif.).

Samples of ten micrograms of cell lysate protein were subjected to a dual luciferase reporter assay according to the manufacturer's instructions (Promega, Wis.). Firefly and *Renilla* luciferase activities were determined in each sample with a luminometer. *Renilla* luciferase activity values in each sample were used to normalize the corresponding IFN γ or IL-2 driven firefly luciferase activity values for variance in transfection efficiency, cell number, cell health, and non-specific changes in transcription. The IFN γ or IL-2 promoter activity for each sample was calculated as a ratio of firefly luciferase to *Renilla* luciferase-dependent luminescence.

Cell viability was determined in approximately 10,000 cells exposed to the experimental treatments described above. After experimental treatment, the cells were incubated in culture medium with tetrazolium salt at 37° C. for four hours. The resulting insoluble products were then collected by centrifugation, dissolved in 100 μL of DMSO and incubated at room temperature for 15 minutes. The formazan reaction product was quantified by optical absorbance at 560 nm. T-cell viability after treatment with a plant extract or a phytocompound was calculated using the following formula: viable cell number (%)=$OD_{560}$ (treated cell culture)/OD560 (control, untreated cell culture)×100.

EXAMPLE 3

Extracts of *B. pilosa* and Centaurein Increased IFN γ and IL-2 Promoter Activity Transfected Jurkat cells carrying pIFN γ-Luc and pRL-TK plasmids were treated with a hot water crude *B. pilosa* extract at various concentrations up to 500 μg/mL or phytohemagglutinin (a known immunostimulant serving as a positive control), or underwent a negative control treatment. The crude extract induced a highly significant increase in IFN γ promoter activity ($p<0.001$) at a concentration of 500 μg/mL.

Fractions obtained from the crude *B. pilosa* extract, described in Example 1 above, were tested for immunostimulant activity. Transfected cells, as described in Example 2 above, were treated with the EA fraction, BuOH fraction, or post-organic solvent extraction water fraction, for 24 hours at various concentrations up to 500 μg/mL. The BuOH fraction induced a highly significant increase in IFN γ promoter activity ($p<0.001$) at the highest concentration tested. In contrast, none of the other fractions significantly increased IFN γ promoter activity. The BuOH fraction-specific immunostimulant activity indicated that the immunostimulant phytocompounds found in the crude *B. pilosa* extract had partitioned primarily into the BuOH fraction.

Centaurein, isolated from the BuOH fraction, was tested for immunostimulant activity in the IFN γ promoter reporter assay described in Example 2 above. Centaurein induced a highly significant increase in ($p<0.001$) at a concentration of 100 μg/mL, relative to the promoter activity in untreated cells. In contrast, 4,5-di-O-caffeoylquinic acid, also isolated from the BuOH fraction, did not induce a significant increase in IFN γ promoter activity.

The BuOH fraction was also tested for its ability to increase IL-2 promoter activity in the assay described in Example 2 above. Treatment with the BuOH fraction at a concentration of 500 μg/mL for 24 hours induced a highly significant increase in IL-2 promoter activity ($p<0.001$) relative to promoter activity in untreated cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of identifying a composition for increasing an immune response, comprising:
providing a recombinant T-cell comprising an expression vector comprising a promoter operably linked to a heterologous reporter sequence encoding a heterologous reporter polypeptide, wherein the promoter of said expression vector consists of SEQ ID NO: 1 and wherein the T-cell expresses the reporter polypeptide;
contacting the T-cell with a test composition; and
assaying an expression level or an activity of the expressed reporter polypeptide, wherein an increase in the expression level or activity of the reporter polypeptide after the T-cell is contacted with the test composition, versus in the absence of the test composition, indicates that the test composition increases an immune response,
wherein the test composition is a plant extract.

2. The method of claim 1, wherein the immune response is an increase in IFN γ promoter activity.

3. The method of claim 1, wherein the reporter polypeptide is selected from the group consisting of firefly luciferase, *renilla* luciferase, fluorescent proteins, β-galactosidase, β-lactamase, alkaline phosphatase, and horseradish peroxidase.

* * * * *

SEQUENCE LISTING

<160> NUMBER OF SEQ ID NOS: 6

<210> SEQ ID NO 1
<211> LENGTH: 615
<212> TYPE: DNA
<213> ORGANISM: Homo sapiens

<400> SEQUENCE: 1

```
ggacttcctc accaaattgt tcttttaacc gcattctttc cttgctttct ggtcatttgc      60
aagaaaaatt ttaaaaggct gcccctttgt aaaggtttga gaggccctag aatttcgttt     120
ttcacttgtt cccaaccaca agcaaatgat caatgtgctt tgtgaatgaa gagtcaacat     180
tttaccaggg cgaagtgggg aggtacaaaa aaatttccag tccttgaatg gtgtgaagta     240
aaagtgcctt caaagaatcc caccagaatg gcacaggtgg gcataatggg tctgtctcat     300
cgtcaaagga cccaaggagt ctaaaggaaa ctctaactac aacacccaaa tgccacaaaa     360
ccttagttat taatacaaac tatcatccct gcctatctgt caccatctca tcttaaaaaa     420
cttgtgaaaa tacgtaatcc tcaggagact tcaattaggt ataaatacca gcagccagag     480
gaggtgcagc acattgttct gatcatctga agatcagcta ttagaagaga agatcagtt      540 aagtcctttg gacctgatca gcttgataca agaactactg atttcaactt ctttggctta    600
attctctcgg aaacg                                                      615

<210> SEQ ID NO 2
<211> LENGTH: 423
<212> TYPE: DNA
<213> ORGANISM: Homo sapiens

<400> SEQUENCE: 2
caccacaata tgctattcac atgttcagtg tagttttatg acaaagaaaa ttttctgagt      60
tacttttgta tccccacccc cttaaagaaa ggaggaaaaa ctgtttcata cagaaggcgt     120
taattgcatg aattagagct atcacctaag tgtgggctaa tgtaacaaag agggatttca     180
cctacatcca ttcagtcagt ctttgggggt ttaaagaaat tccaaagagt catcagaaga     240
ggaaaaatga aggtaatgtt ttttcagaca ggtaaagtct ttgaaaatat gtgtaatatg     300
taaaacattt tgacaccccc ataatatttt tccagaatta acagtataaa ttgcatctct     360
tgttcaagag ttccctatca ctctctttaa tcactactca cagtaacctc aactcctgcc     420
aca                                                                   423

<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
ggacttcctc accaaattgt t                                                21

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
cgtttccgag agaattaagc c                                                21

<210> SEQ ID NO 5
<211> LENGTH: 29
<212> TYPE: DNA
<213> ORGANISM: Artificial Sequence
<220> FEATURE:
<223> OTHER INFORMATION: Primer
```

```
<400> SEQUENCE: 5
cggggtaccc accacaatat gctattcac                                29

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
gccggtacct gtggcaggag ttgaggttac                               30
```